United States Patent
Witham et al.

(10) Patent No.: US 7,229,195 B2
(45) Date of Patent: Jun. 12, 2007

(54) LAMP STANDARD

(75) Inventors: David L. Witham, Ventura, CA (US); Robert Arance, Valencia, CA (US)

(73) Assignee: Ultraviolet Devices, Inc., Valencia, CA (US)

( * ) Notice: Subject to any disclaimer, the term of this patent is extended or adjusted under 35 U.S.C. 154(b) by 0 days.

(21) Appl. No.: 11/286,867

(22) Filed: Nov. 23, 2005

(65) Prior Publication Data

US 2006/0072318 A1 Apr. 6, 2006

Related U.S. Application Data

(63) Continuation of application No. 10/677,969, filed on Oct. 1, 2003, now Pat. No. 6,979,103.

(51) Int. Cl.
*F21V 33/00* (2006.01)

(52) U.S. Cl. .................. 362/234; 362/147; 362/217; 362/249; 362/285

(58) Field of Classification Search ................ 362/234, 362/147, 153, 217, 219, 225, 249, 252, 285, 362/396, 431, 432; 248/158, 122.1

See application file for complete search history.

(56) References Cited

U.S. PATENT DOCUMENTS

| | | | | | |
|---|---|---|---|---|---|
| 2,413,704 | A | * | 1/1947 | Glatthar et al. | 250/435 |
| 3,737,834 | A | * | 6/1973 | Contratto | 439/118 |
| 4,646,211 | A | * | 2/1987 | Gallant et al. | 362/149 |
| 5,902,034 | A | * | 5/1999 | Santosuosso et al. | 362/125 |
| 6,183,112 | B1 | * | 2/2001 | Bomas | 362/285 |

\* cited by examiner

*Primary Examiner*—Sandra O'Shea
*Assistant Examiner*—Mark Tsidulko
(74) *Attorney, Agent, or Firm*—Cislo & Thomas LLP

(57) ABSTRACT

A lamp standard for mounting in an air handling system composed of a stand having a plurality of channels wherein the channels span along the longitudinal axis of the stand and a plurality of lamp modules positioned over the channels. The lamp modules include a housing, a lamp bulb extending from the housing, and the wiring associated with the lamp modules are positioned within the channels. In use, the lamp standard can be installed within a heating, ventilation, or air conditioning (HVAC) system to minimize airborne and/or surface microorganism contaminants. The ultraviolet dosage delivered to the HVAC system can be controlled by varying the number of lamp standards, number of lamp modules coupled to the lamp standards, and spacing between the individual lamp standards.

11 Claims, 5 Drawing Sheets

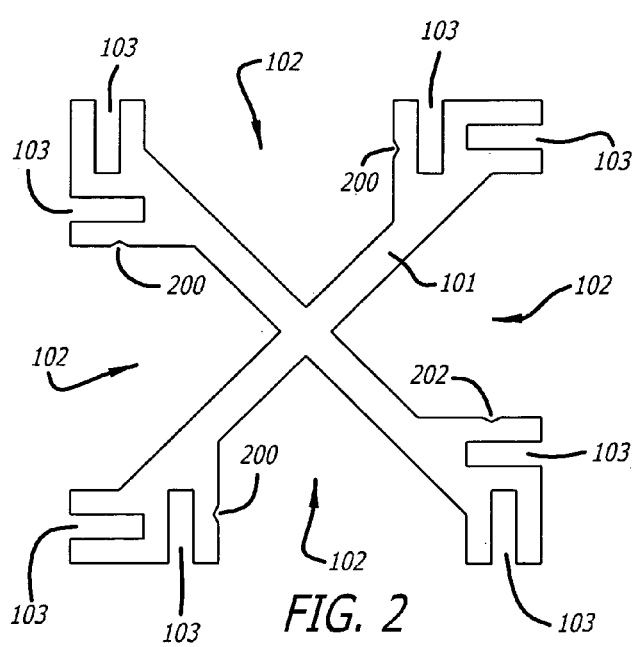
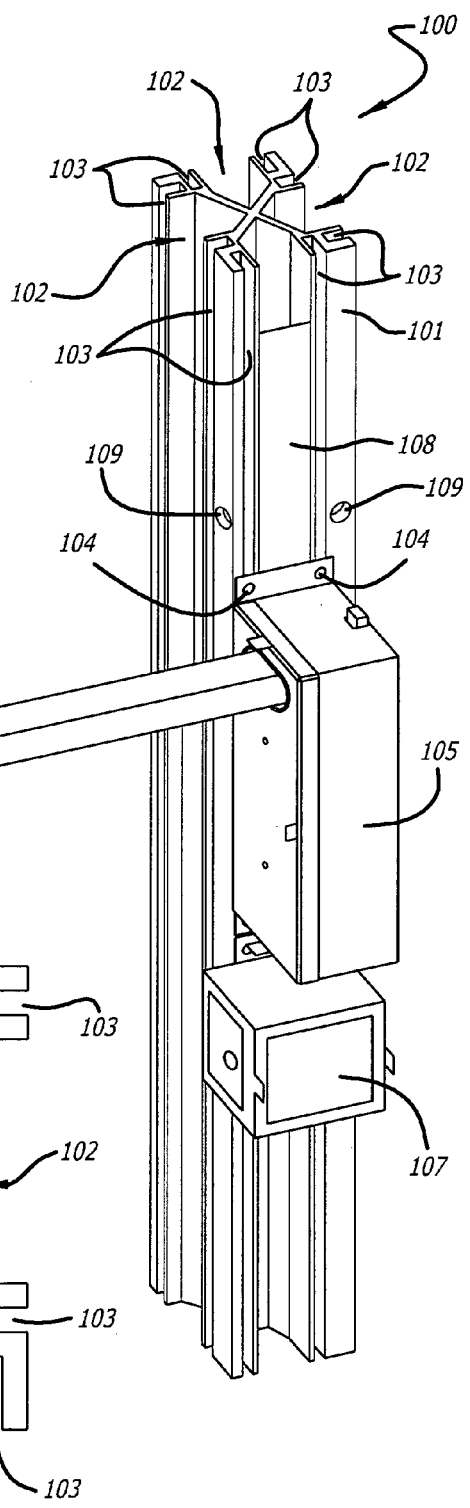
FIG. 1
FIG. 2

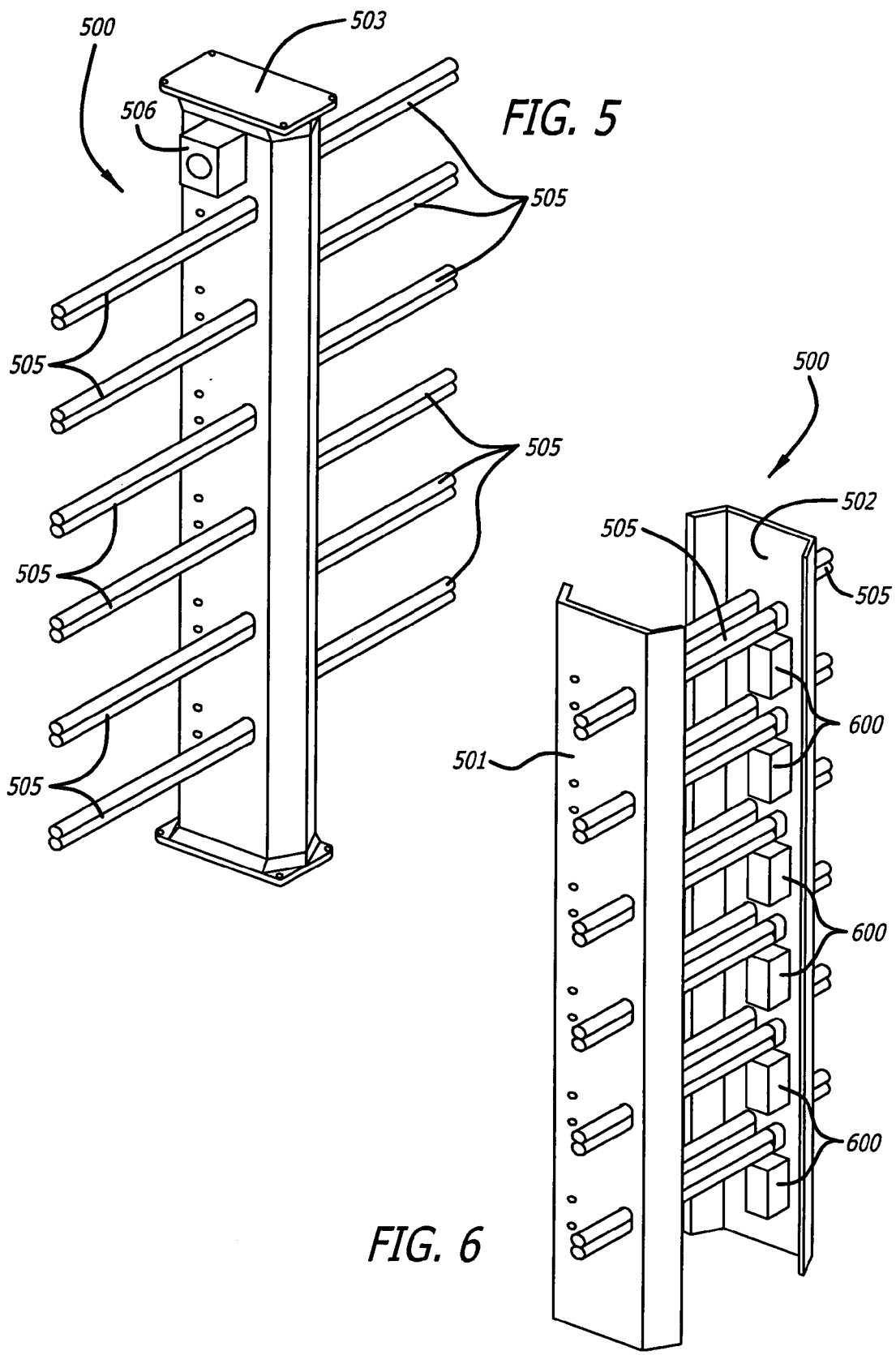

LAMP STANDARD

CROSS-REFERENCES TO RELATED APPLICATIONS

This patent application is a continuation application of U.S. patent application Ser. No. 10/677,969 filed Oct. 1, 2003 for ULTRAVIOLET LAMP STANDARDS AND METHODS OF USE THEREOF, which application is incorporated herein by this reference thereto.

BACKGROUND

Ultraviolet (UV) light energy has long been used in the disinfection of water, surfaces and air. The mechanism of disinfection and the effects that UV energy, particularly that in the UVC-germicidal wavelengths, is well understood. Recently, more UV applications have been made in HVAC equipment. HVAC equipment can range from small, stand-alone air cleaners to large commercial and industrial systems for buildings. In large systems, UV lamps can be mounted on rooftops or in equipment rooms.

Typically, these systems contain an air handling unit (fan), heating components such as electric coils or heat exchangers, air-conditioning coils, air filter elements, and the necessary enclosure and duct work to bring building and outside air into the equipment and deliver it back to the building. UV light can then be applied at several locations within this HVAC system. Common locations may be near the filters, near surfaces which may harbor mold and bacteria, near air-conditioning coils, near drain pans and possibly in a cross-section of the duct to disinfect the moving air stream.

Depending upon the application, the UV lamp fixtures can be mounted individually within the system or exterior to the ductwork incorporating fixtures that have the lamp itself protruding into the ductwork. Also, in some applications, the ballasts that power the lamps can be located within the duct and enclosed in a fixture. In many applications, the ballasts can be located external to the duct and connected to the lamps via wiring and conduit. Installations of these UV lamps are often complex and costly because the lamp fixtures typically require individual mounting and a separate supporting frame structure. Wiring these lamps can also be complex and costly as each lamp or lamp fixture via wire and conduit to operate. In addition, complex framework and fixture mounting can partially block the air paths that can contribute to loss of airflow and pressure drop.

SUMMARY

Exemplary embodiments disclosed herein are directed to lamp standards that may be fixed within an HVAC system. According to one exemplary embodiment, the lamp standard is composed of a stand body that may have one or more lamp modules mounted thereon. The channels span the length of the lamp standard, which allow the lamp modules to be mounted at any point on the stand body. The stand body includes a plurality of channels that is sized to house the wiring associated with the lamp modules. More specifically, the base of the lamp module and the walls of the channels define an enclosed space that house the wiring associated with the lamp modules and ballasts. Accordingly, this enclosed space protects the writing from the harmful effects of the UV light emitted from the lamp bulbs.

In another exemplary embodiment, the lamp standard is composed of a stand body having a first body shell and a second body shell. The first and second body shells may be coupled together to define an enclosure. Within the enclosure, the lamp modules and the power modules may be housed therein. The body shells also include a plurality of openings that are sized to allow the lamp bulbs associated with the lamp modules to extend away from the lamp standard. The wiring associated with the lamp modules and ballasts are contained within the enclosure of the lamp standard.

Accordingly, the various embodiments of the lamp standard provides a means of providing UV lamps within a heating, ventilation, and air conditioning (HVAC) system. The lamp standards have a generally low profile thereby minimizing airflow blockage. Also, the lamp standards are modular and can be adapted for various applications requiring differing UV dosages for a given area. Futhermore, by providing an enclosure within the lamp standard, the wiring associated with the lamp standard may be protected from the harmful effects of UV light and radiation.

BRIEF DESCRIPTION OF THE DRAWINGS

FIG. 1 is an exemplary embodiment of a lamp standard;

FIG. 2 is a cross-sectional view of the lamp standard of FIG. 1;

FIG. 5 is another exemplary embodiment of a lamp standard;

FIG. 6 is an exploded perspective view of a portion of the lamp standard of FIG. 5.

DETAILED DESCRIPTION

Figure 3:
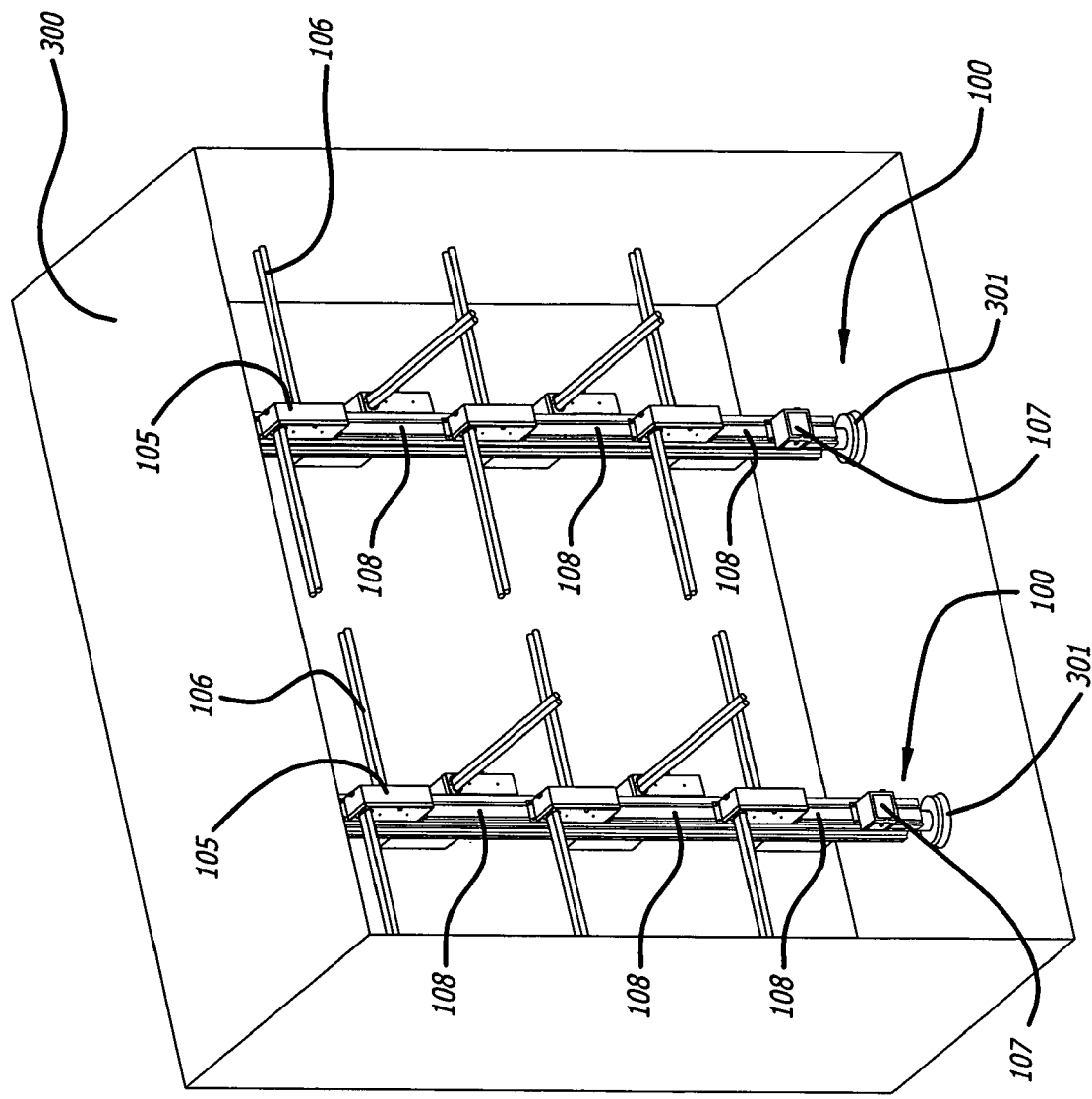
FIG. 3 is a perspective view of an exemplary embodiment wherein the lamp standard of FIG. 1 is installed within a HVAC system.

The detailed description set forth below in connection with the appended drawings is intended as a description of exemplary embodiments and is not intended to represent the only forms in which the exemplary embodiments may be constructed and/or utilized. The description sets forth the functions and the sequence of steps for constructing and operating the exemplary embodiments in connection with the illustrated embodiments. However, it is to be understood that the same or equivalent functions and sequences may be accomplished by different embodiments that are also intended to be encompassed within the spirit and scope of the invention.

FIG. 1 illustrates an exemplary embodiment of a lamp standard 100. Broadly, the lamp standard 100 may be composed of a stand body 101, a plurality of lamp modules 105 coupled to the stand body 101, and one or more power modules 107. As shown in FIG. 1, the stand body 101 has a generally X-shaped cross-section formed from intersecting walls. The intersecting walls of the stand body 101 define a plurality of channels 102. As shown in FIGS. 1–2, the stand body 101 has a generally X-shaped cross-section to define a polygonal structure. More specifically, the lamp stand body 101, as depicted in FIGS. 1 and 2, depict a generally square perimeter. Accordingly, lamp modules 105 may be placed on one or more of the four sides of the lamp stand 101. As those skilled in the art will appreciate, two or more walls may be used to define a plurality of polygonal shapes such as a triangle, a rectangle, a pentagon, or other shapes known in the art.

As shown in the exemplary embodiment of FIG. 1, the channel 102 is generally V-shaped. In alternate embodiments, the channels 102 may be rectangular or otherwise shaped to define a channel. The channels 102 are sized to house wires (not shown) that are associated with the lamp module 105 and the power module 107. The channels 102 may be substantially adjacent to one another as well as substantially centered upon the longitudinal axis of the stand. The stand body 101 also includes a plurality of grooves 103 that span along the longitudinal axis of the stand body 101 and are adjacent to the channel 102. As shown in FIG. 1, the grooves 103 are continuous along the length of the stand body 101, but in an alternate embodiment, the grooves may be intermittent (i.e., span shorter distances). The stand body 101 may also include a through-hole 109 that allows for the power source wiring (not shown) to be coupled to the power module 107. As shown in FIG. 2, the stand body 101 may include a plurality of notches 200 that are provided within the channels 102. The notches 200 are positioned such that they are in-line with an opposing corner of the channel 102.

Turning back to FIG. 1, the lamp module 105 is fastened to the stand body 101 by fastening members 104. In one exemplary embodiment, the fastening members 104 may be screws. As those skilled in the art will appreciate, the fastening members 104 may be bolts, clamps, and/or other coupling means. According to one exemplary embodiment, the lamp module 105 is secured to the lamp stand body 101 and is configured such that the lamp bulb 106 extends from a lamp module such that it is perpendicular to the longitudinal axis of the stand body 101. In an alternate embodiment, as those skilled in the art will appreciate, the lamp module 105 may be configured such that the lamp bulb 106 extends from the lamp module 105 in a direction that is substantially parallel to the longitudinal axis of the stand body 101. In yet another exemplary embodiment, the lamp module 105 may be configured such that the lamp bulb 100 extends from the lamp module 105 at an angle.

Additionally, one or more power modules 107 may also be coupled to the stand body 101. The power modules 107 may be electrically coupled to one or more lamp modules 105. According to one exemplary embodiment, the power module 107 may be able to accommodate one to twenty-four lamp modules 105. However, as those skilled in the art will appreciate, other exemplary embodiments of the power module 107 may be utilized that can handle more than twenty-four lamp modules 105.

Additionally, as shown in FIG. 1, a plate 108 may be placed within the channel of the stand body 101. In alternate embodiments, the plate 108 may be secured over the channel via screws along the grooves 103. The plates 108 provide protection for the wiring looms for the various lamp modules from the potentially degradative effects of the UV light. That is, the plate 108 may be inserted into the notch 200 and the opposing corner to cover the wires in one exemplary embodiment.

FIG. 3 illustrates two lamp standards 100 that are fixed in an HVAC system. The lamp standards 100 are secured in the HVAC system by a lower mounting bracket 301 and an upper mounting bracket (not shown). Additionally, FIG. 3 illustrates an exemplary embodiment where the lamp standard 100 has a plurality of lamp modules 105 mounted thereon and coupled to a power module 107. The lamp modules 105 are situated on the lamp stand body 101 such that the lamp bulbs 106 extend along the x-axis and the z-axis of the HVAC vent. In other exemplary embodiments, the lamp standard 100 may include lamp modules 105 that have lamp bulbs 106 that only extend in the x-axis, the y-axis, or the z-axis, or combinations thereof.

Figure 4:
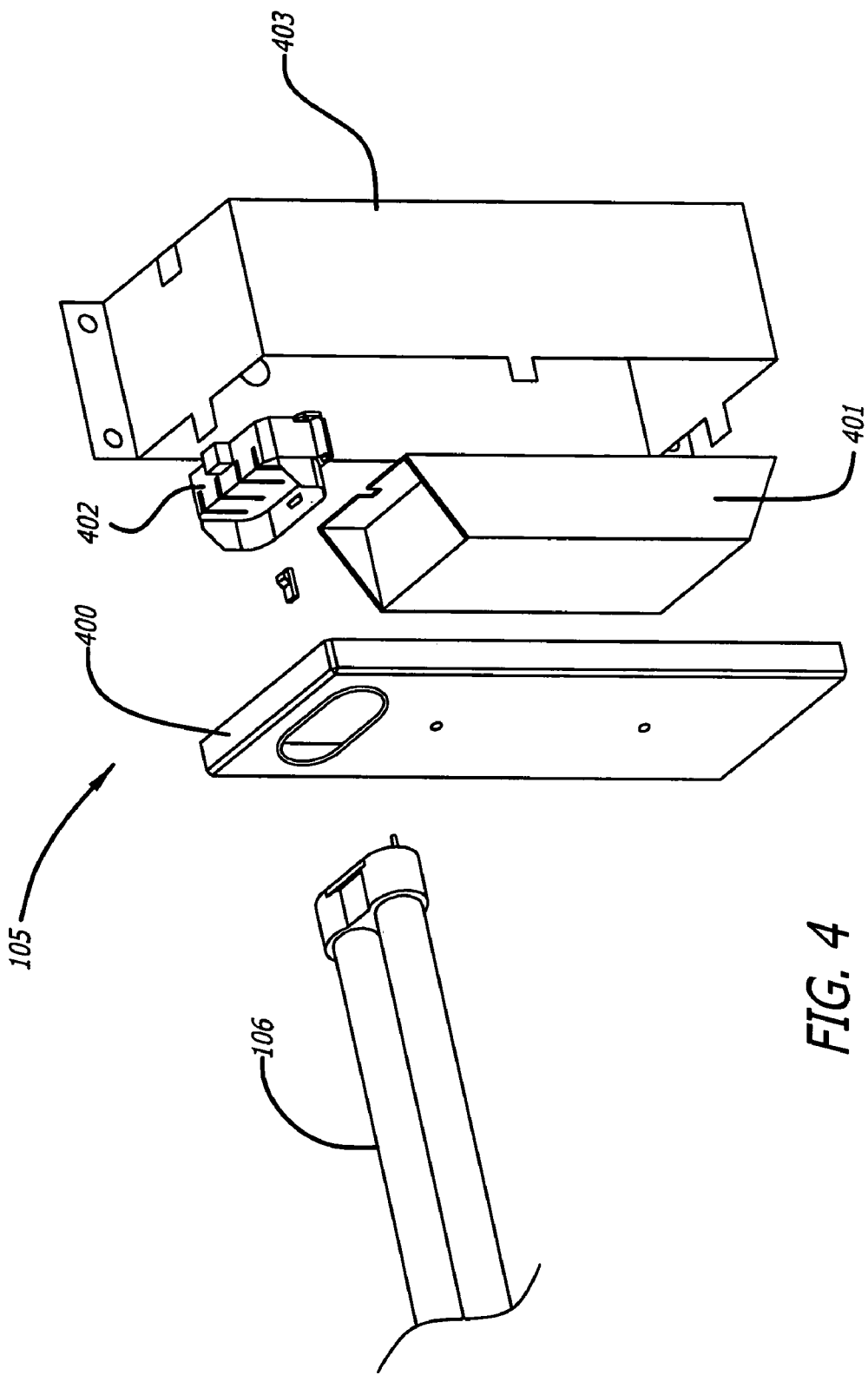
FIG. 4 is an exploded perspective view of an exemplary lamp module.

FIG. 4 illustrates an exploded view of the lamp module 105. The lamp module comprises a cover 400 and a housing 403. The housing is a generally rectangular structure that defines a cavity that is capable of holding within the lamp module 105, a lamp bulb plug 402 and a means 401 for supplying power to the lamp bulbs is provided therein. As those skilled in the art will appreciate, the lamp bulb plug 402 may be substituted to accommodate the various types of lamp bulbs 106 that are known or used in the art. According to one exemplary embodiment, the lamp bulb 106 may be an ultraviolet lamp bulb. In another exemplary embodiment, the lamp bulb 106 may be a UV-C germicidal lamp. Additionally, as shown in FIG. 1, the lamp bulb 106 is a double-tube, double-ended lamp bulb. In another exemplary embodiment, the lamp bulb 106 may be a single-tube, single-ended lamp.

FIGS. 5–6 illustrate another exemplary embodiment of a lamp standard 500. The lamp standard 500 is composed of a first body shell 501 and a second body shell 502. The first and second body shells 501, 502 may be coupled together to define a cavity (as shown in FIG. 6) in which to house the lamp modules 600 and power modules 806. The body shells 501, 502 may be coupled together with fasteners such as, but not limited to, screws, rivets, or the like. The body shells 501, 502 may be mirror images of each other and may be made from sheet metal. In other embodiments, the body shells 501, 502 may be made from tubing and/or extrusions. In an alternate embodiment, the power module 506 may be positioned on the outside of the lamp standard 500. In various exemplary embodiments, the power modules 506 may be electronic or magnetic ballasts.

Figure 7:
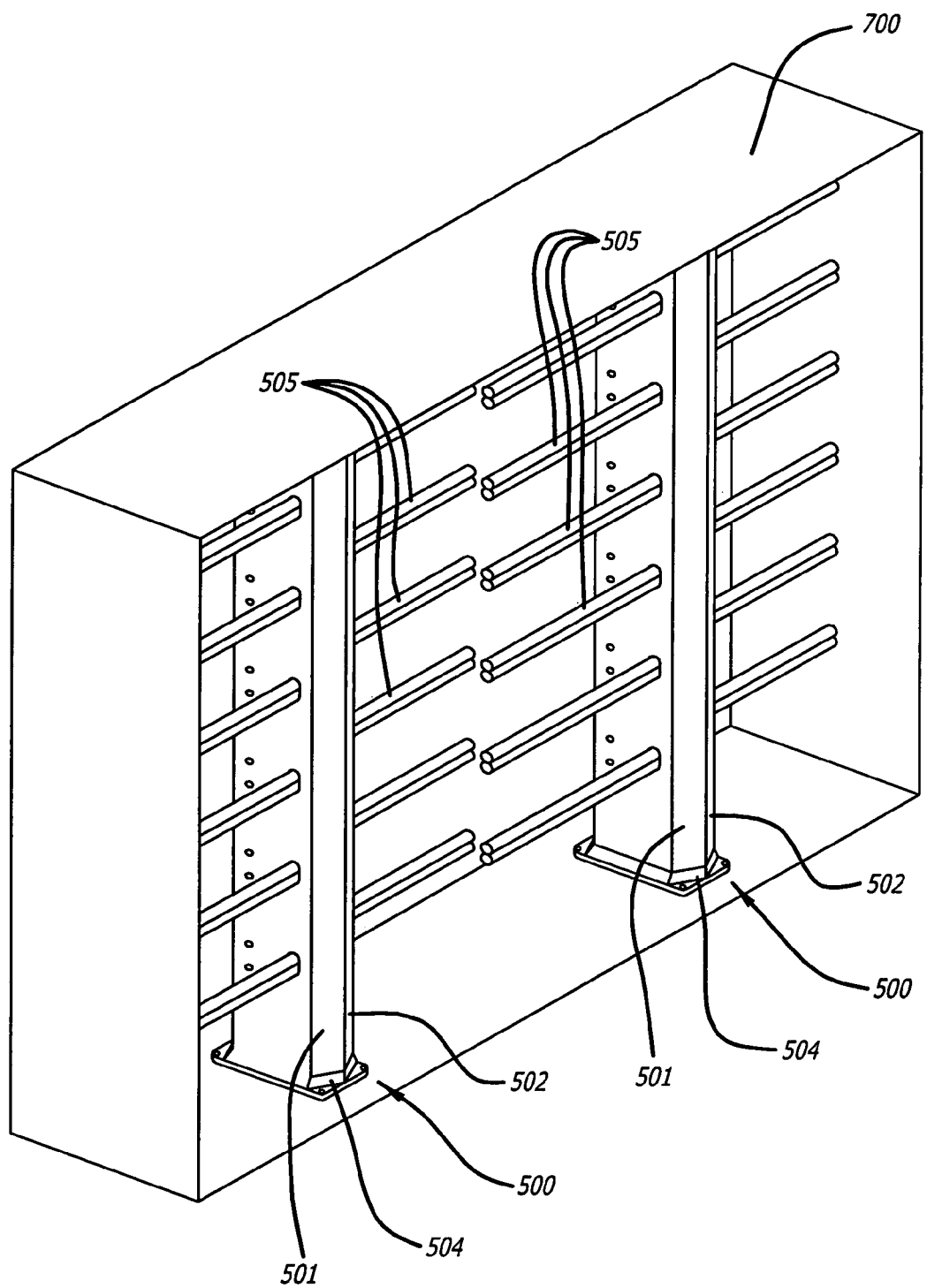
FIG. 7 is a perspective view of an exemplary embodiment of the lamp standard of FIG. 5 installed within a HVAC system.

Additionally, a plurality of openings are spaced along the length of the body shells 501, 502. These openings are sized to allow the lamp bulbs 505 to protrude therethrough. According to one exemplary embodiment, lamp bulbs 505 are staggered as shown in FIG. 5. In alternate embodiments, the lamp standard 500 may be configured such that the opposite lamp bulbs 505 are substantially planar. As shown in FIG. 5, the lamp standard 500 is capable as shown to house six pairs of lamp bulbs 505. In alternative embodiments, the lamp standards may be sized to house one or more lamp bulbs depending on the intended application or duct size. The lamp standard may also include a top-mounting bracket 503 and a bottom-mounting bracket 504 to provide at the ends of the lamp standard 500 and facilitate the installation of the lamp standard 500 within HVAC ducting 700, as illustrated in FIG. 7.

In another aspect, exemplary methods of using the lamp standards are disclosed herein. According to the exemplary methods, the various embodiments of the lamp standard may be used in forced air heating and/or cooling systems to minimize airborne and/or surface microorganism contaminants. In one exemplary method, the lamp standard may be mounted in a duct for airborne applications. In another exemplary method, the lamp standard may be mounted in a duct for surface applications. The lamp standard is mounted within the duct that prevents exposure to components such as, but not limited to, plastic flexible duct components, polyurethane foam insulation material, rubber hoses, and wire insulation. If mounting options are limited, UV sensitive materials can be protected with UV resistant material such as, but not limited to, aluminum foil, aluminum duct tape, metallic shields, or the like. Additionally, the lamp standard should be located within the duct such that the lamp standard brackets may be mounted on the floor and the ceiling of the duct.

Once the location is determined, the UV dosage required for the desired location is determined. The desired UV dosage is determined by the number of lamp modules (and concomitantly number of lamp bulbs) and the number of lamp standards required for the space within the duct. For surface applications, if more than one lamp standard is required for the intended application, the distance between lamp standards is approximately 32 inches and the space between rows of lamp bulbs is approximately 12 inches to approximately 18 inches. If more than one lamp standard is required for the intended application, the distance between lamp standards is approximately 32 inches and the space between rows of lamp bulbs is approximately 24 inches for surface applications. As those skilled in the art will appreciate, other factors such as air temperature within the duct, air velocity, and duct reflectivity are also taken into consideration when ascertaining proper UV dosage.

While the present invention has been described with regards to particular embodiments, it is recognized that additional variations of the exemplary embodiments may be devised without departing from the inventive concept.

What is claimed is:

1. An ultraviolet light lamp standard for mounting in an air handling system, comprising:
   a stand having a plurality of substantially adjacent, elongate, spaced channels, wherein said channels are substantially centered upon and span along the longitudinal axis of the stand; and
   a plurality of lamp modules positioned over the channels, wherein the lamp modules comprise a housing and an ultraviolet light lamp bulb extending from the housing, and wherein wiring associated with said lamp modules are positioned within the channels, said lamp modules being adapted for positioning in one of parallel and perpendicular positions relative to said longitudinal axis of said stand.

2. The ultraviolet lamp standard of claim 1 wherein stand further comprises a first groove and a second groove, wherein the first groove and second groove are positioned on opposite sides of the channels.

3. The ultraviolet lamp standard of claim 2 further comprising a top mounting bracket and bottom mounting bracket coupled to a top end and a bottom end of the stand, respectively.

4. The ultraviolet lamp standard of claim 3 further comprising one or more power junction modules coupled to the stand, wherein the one or more power modules are electrically coupled to the plurality of lamp modules.

5. The ultraviolet lamp standard of claim 3 wherein said modules are selectively positionable along the extent of said elongate, spaced channels.

6. The ultraviolet lamp standard of claim 5 wherein said plurality of lamp modules are configured so that the ultraviolet light lamp bulbs are nonplanar.

7. The ultraviolet lamp standard of claim 1 wherein the plurality of lamp modules are configured so that the ultraviolet light lamp bulbs are coaxial.

8. The ultraviolet lamp standard of claim 1 wherein the stand further comprises at least one through hole positioned on at least one end of the stand.

9. The ultraviolet lamp standard of claim 1 wherein the plurality of channels are generally V-shaped.

10. An ultraviolet lamp standard for mounting in an air handling system, comprising:
    an elongate stand having a first wall intersecting a second wall to form a first pair of opposing channels and a second pair of opposing channels, wherein the first pair and the second pair of channels span along a longitudinal axis of the elongate stand;
    a plurality of ultraviolet lamp modules releasably coupled over the channels to thereby define an enclosed space, wherein the ultraviolet lamp modules comprise a housing and an ultraviolet lamp bulb extending to from the housing; and
    one or more power junction modules coupled to the stand, wherein the one or more power modules are electrically coupled to the plurality of ultraviolet lamp modules.

11. An ultraviolet lamp standard for mounting in an air handling system as set forth in claim 10, further comprising:
    a top mounting bracket and bottom mounting bracket coupled to a top end and a bottom end of the stand, respectively.

* * * * *